(12) United States Patent
Kwon et al.

(10) Patent No.: US 11,979,650 B2
(45) Date of Patent: May 7, 2024

(54) IMAGE ACQUISITION DEVICE FOR DIAGNOSING AND ANALYZING STATE OF A TARGET

(71) Applicant: MEDIVEL BIO CO., LTD., Seoul (KR)

(72) Inventors: Bo Sun Kwon, Seoul (KR); Jun Hwan Lee, Seoul (KR)

(73) Assignee: MEDIVEL BIO CO., LTD., Seoul (KR)

( * ) Notice: Subject to any disclaimer, the term of this patent is extended or adjusted under 35 U.S.C. 154(b) by 205 days.

(21) Appl. No.: 17/627,263

(22) PCT Filed: Mar. 9, 2020

(86) PCT No.: PCT/KR2020/003289
§ 371 (c)(1),
(2) Date: Jan. 14, 2022

(87) PCT Pub. No.: WO2021/010568
PCT Pub. Date: Jan. 21, 2021

(65) Prior Publication Data
US 2022/0263982 A1     Aug. 18, 2022

(30) Foreign Application Priority Data
Jul. 15, 2019   (KR) ........................ 10-2019-0085140

(51) Int. Cl.
*H04N 23/54*     (2023.01)
*H04N 23/51*     (2023.01)
*H04N 23/56*     (2023.01)

(52) U.S. Cl.
CPC ............. *H04N 23/54* (2023.01); *H04N 23/51* (2023.01); *H04N 23/56* (2023.01)

(58) Field of Classification Search
CPC ........ H04N 23/54; H04N 23/51; H04N 23/56; A61B 5/442; A61B 2560/0431;
(Continued)

(56) References Cited

U.S. PATENT DOCUMENTS

2015/0148686 A1*   5/2015   Baym ................. A61M 35/003
                                                                     600/572
2016/0342822 A1*   11/2016   Lei ....................... G06K 7/1413
(Continued)

FOREIGN PATENT DOCUMENTS

| CN | 104883970 A | 9/2015 |
|---|---|---|
| CN | 106175670 A | 12/2016 |

(Continued)

OTHER PUBLICATIONS

International Search Report for PCT/KR2020/003289 dated Jun. 16, 2020.

(Continued)

*Primary Examiner* — Hung H Lam
(74) *Attorney, Agent, or Firm* — Sughrue Mion, PLLC

(57) ABSTRACT

An image acquisition device according to an embodiment includes: a body; a seat part provided on a lower part of the body; a substrate disposed on the seat part inside the body and having a plurality of light sources; and a light source angle forming part disposed on the substrate inside the body. The substrate may be provided on the seat part in the form of a planar plate, and an outer peripheral portion of the substrate may be bent so that the light sources are directed toward one focal point by the seat part and the light source angle forming part.

10 Claims, 6 Drawing Sheets

(58) Field of Classification Search
CPC .................. A61B 5/0059; A61B 5/443; A61B 2562/0247; A61B 5/01; A61B 2562/0261; A61B 2562/0271; A61B 2562/029; A61B 2562/04
See application file for complete search history.

(56) References Cited

U.S. PATENT DOCUMENTS

| | | | | |
|---|---|---|---|---|
| 2019/0059857 | A1* | 2/2019 | Ogura | A61B 8/0858 |
| 2019/0090751 | A1 | 3/2019 | Hwang et al. | |
| 2019/0117497 | A1* | 4/2019 | Sedic | A61H 23/006 |
| 2020/0060608 | A1* | 2/2020 | Choi | A61B 5/441 |

FOREIGN PATENT DOCUMENTS

| | | |
|---|---|---|
| CN | 107374592 A | 11/2017 |
| CN | 109219389 A | 1/2019 |
| EP | 1 464 165 B1 | 4/2007 |
| JP | 2018-175848 A | 11/2018 |
| KR | 10-2009-0032128 A | 3/2009 |
| KR | 10-1274303 B1 | 6/2013 |
| KR | 10-2017-0138139 A | 12/2017 |
| KR | 10-2018-0010295 A | 1/2018 |
| KR | 10-2018-0132914 A | 12/2018 |
| KR | 10-2064971 B1 | 1/2020 |
| WO | 2016/204432 A1 | 12/2016 |

OTHER PUBLICATIONS

Written Opinion for PCT/KR2020/003289 dated Jun. 16, 2020.
Communication dated Aug. 19, 2023, issued in Chinese Application No. 202080051269.6.
Communication dated Aug. 2, 2023, issued in European Application No. 20841416.9.

* cited by examiner (a)

(b)

(c)

IMAGE ACQUISITION DEVICE FOR DIAGNOSING AND ANALYZING STATE OF A TARGET

CROSS REFERENCE TO RELATED APPLICATIONS

This application is a National Stage of International Application No. PCT/KR2020/003289 filed Mar. 9, 2020, claiming priority based on Korean Patent Application No. 10-2019-0085140 filed Jul. 15, 2019.

TECHNICAL FIELD

Proposed is an image acquisition device. Specifically, proposed is a device capable of acquiring an image to analyze a state of a target and simultaneously measuring a characteristic of the target by means of contact and pressure of a sensor.

BACKGROUND ART

In general, spectral imaging and spectral image analysis techniques can obtain information on a target, such as a tissue, non-invasively, and thus are useful in diagnosing and analyzing various characteristics of the target. For spectroscopic imaging to obtain information on a target, light beams from a plurality of light sources have to pass through a filter, and then the light beams from the filter have to pass through a polarizing film to be focused on a location of the target. In this case, in order to simultaneously obtain various information on the same target, such a plurality of light sources are required, and light beams from the plurality of light sources need to be focused to one focal point. In addition, in order to more broadly diagnose and analyze the characteristics of the target, it is necessary to provide various types of sensors.

As a related technology, Korean Patent Application Publication No. 10-2009-0032128 discloses a "MULTIBIOMETRIC MULTISPECTRAL IMAGER"

DISCLOSURE

Technical Problem

Accordingly, the present disclosure has been made keeping in mind the above problems occurring in the related art, and an objective of the present disclosure is to provide an image acquisition device for easily diagnosing and analyzing a state of a target.

Another objective according to an embodiment is to provide an image acquisition device for easily measuring characteristics such as temperature, oil/moisture, or elasticity of a target.

Another objective according to an embodiment is to provide an image acquisition device for adjusting an angle of light sources during assembly so that light paths of the light sources intersect with each other toward one focal point.

Another objective according to an embodiment is to provide an image acquisition device that is free from time or location restrictions in diagnosing, measuring, and analyzing a state or characteristic of a target.

Another objective according to an embodiment is to provide an image acquisition device that can be mounted on a portable terminal.

Another objective according to an embodiment is to provide an image acquisition device capable of simultaneously measuring various characteristics of a target through one contact part.

Objectives to be achieved in the embodiments are not limited to those mentioned above, and other objectives not mentioned will be clearly understood by those skilled in the art from the following description.

Technical Solution

In order to accomplish the above objectives, an image acquisition device according to an embodiment may include: a body; a seat part provided on a lower part of the body; a substrate disposed on the seat part inside the body and having a plurality of light sources; and a light source angle forming part disposed on the substrate inside the body. The substrate is provided on the seat part in the form of a planar plate, and an outer peripheral portion of the substrate is bent so that the light sources are directed toward one focal point by the seat part and the light source angle forming part.

According to an aspect, the plurality of light sources may be disposed on the outer peripheral portion of the substrate, and the outer peripheral portion of the substrate may be bent so that light paths of the light sources intersect with each other by the seat part or the light source angle forming part.

According to an aspect, the seat part may be formed at a position corresponding to each of the plurality of light sources, and may have a triangular cross-section.

According to an aspect, the light source angle forming part may have an inclined surface corresponding to each seat part, and a through-hole allowing each of the plurality of light sources to pass therethrough.

A method of manufacturing an image acquisition device according to an embodiment may include: providing a lower part of the body provided with a triangular seat part; providing, on the seat part, a planar substrate provided with a plurality of light sources; providing, on the substrate, a light source angle forming part having an inclined surface; and bending an outer peripheral portion of the substrate so that the light sources of the substrate is directed toward one focal point with respect to the seat part while the light source angle forming part presses the substrate.

According to an aspect, the method may further include: providing a film receiving part on the light source angle forming part and fastening the film receiving part to the lower part of the body together with the light source angle forming part and the substrate.

An image acquisition device according to another embodiment may include: an image acquisition module configured to measure a state of a target; a measurement module configured to measure at least one target characteristic of elasticity, temperature, and oil/moisture; and a body in which the image acquisition module and the measurement module are mounted. A portion of the measurement module may protrude to outside of the body and may measure the characteristic of the target by making direct contact with the target.

According to an aspect, the measurement module may include: a base fixed to the body; a contact member passing through the base and configured to make direct contact with the target and having a first sensor therein; an elastic member having a first end coupled to a lower end of the contact member; and a support member having a first end coupled to a second end of the elastic member and having a second end in contact with a second sensor. The first sensor may measure the temperature or the oil/moisture of the target, and the second sensor may measure the elasticity of the target from pressure transmitted through the support member when the contact member makes contact with the target.

According to an aspect, the measurement module may include: a base fixed to the body; a first measuring part mounted to the base and configured to measure the temperature of the target; a second measuring part mounted to the base, disposed adjacent to the first measuring part, and configured to measure the oil/moisture of the target; and a third measuring part mounted to the base, disposed adjacent to the first measuring part or the second measuring part, and configured to measure the elasticity of the target. Each of the first measuring part, the second measuring part, and the third measuring part may measure the characteristic of the target by making contact with the target.

According to an aspect, the first measuring part may include a first contact member protruding to outside of an upper part of the body and configured to make direct contact with the target, and the first contact member may be provided with a temperature sensor to measure the temperature of the target.

According to an aspect, the second measuring part may include: a second contact member protrudes to outside of an upper part of the body by passing through the base and configured to make direct contact with the target; an elastic member having a first end coupled to a lower end of the second contact member; and a support member to which a second end of the elastic member is coupled. The second contact member may be provided with an oil/moisture sensor to measure the oil/moisture of the target.

According to an aspect, the third measuring part may include: a third contact member protruding to outside of an upper part of the body by passing through the base and configured to make direct contact with the target; an elastic member having a first end coupled to a lower end of the third contact member; and a support member having a first end coupled to a second end of the elastic member and a second end in contact with a pressure sensor. The elasticity of the target may be measured from pressure generated when the third contact member makes contact with the target is transmitted to the pressure sensor through the support member.

Advantageous Effects

According to an image acquisition device according to an embodiment, it is possible to easily diagnose and analyze a state of a target.

According to the image acquisition device according to the embodiment, it is possible to easily measure characteristics of a target, such as temperature, oil/moisture, elasticity, or the like.

According to the image acquisition device according to the embodiment, it is possible to adjust an angle of light sources during assembly so that light paths of the light sources intersect with each other toward one focal point.

According to the image acquisition device according to the embodiment, it is possible to diagnose, measure, and analyze a state or characteristic of a target without time or location restrictions.

According to the image acquisition device according to the embodiment, it is possible to mount the device on a portable terminal.

According to the image acquisition device according to the embodiment, it is possible to simultaneously measure various characteristics of a target through one contact part.

Effects of the image acquisition device according to the embodiment are not limited to those mentioned above, and other effects not mentioned will be clearly understood by those skilled in the art from the following description.

Figure 1:
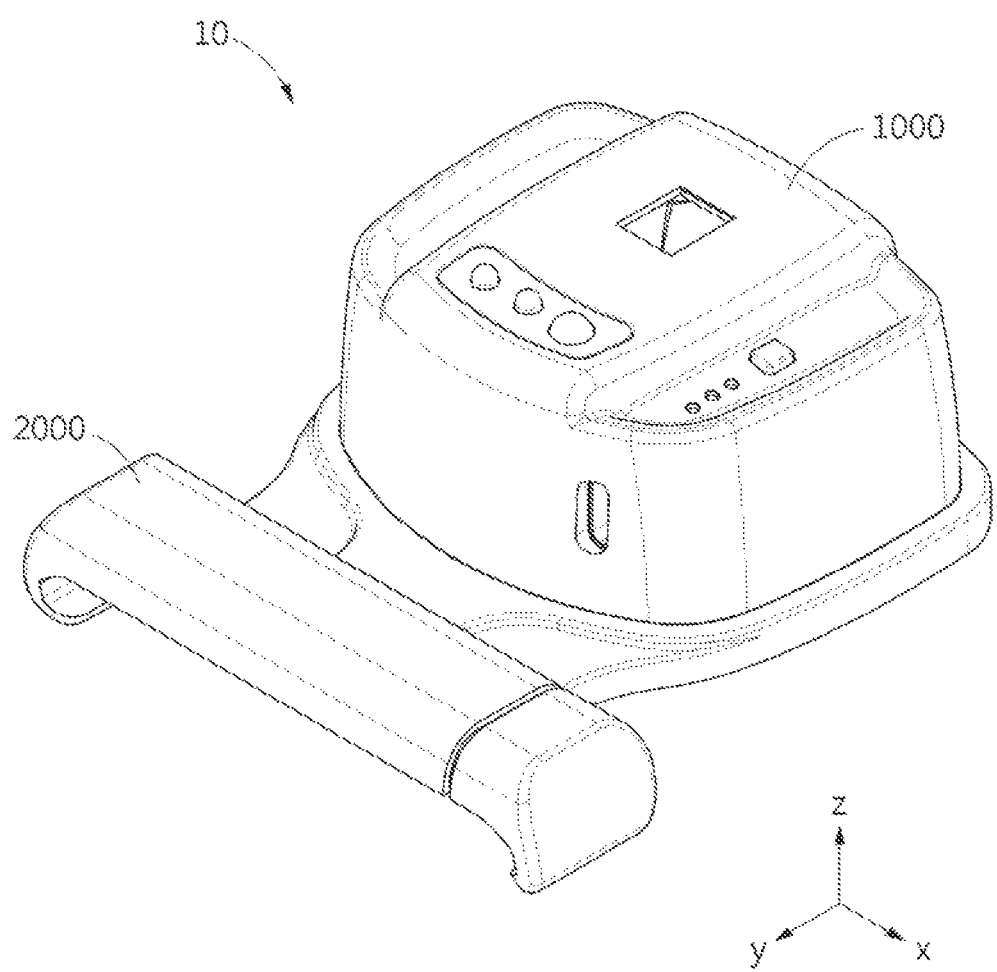
FIG. 1 is a perspective view illustrating an image acquisition device.

The accompanying drawings illustrate a preferred embodiment of the present disclosure and, together with the description, serve to explain the principles of the disclosure. Accordingly, the scope of the present disclosure should not be construed as being limited to the embodiment illustrated in the drawings.

BEST MODE

Hereinafter, embodiments will be described in detail with reference to exemplary drawings. Like reference numerals are used to identify like elements throughout different drawings. Further, in the following description, if it is decided that the detailed description of known function or configuration related to the disclosure makes the subject matter of the disclosure unclear, the detailed description is omitted.

Further, when describing the components of the present disclosure, terms such as first, second, A, B, (a), or (b) may be used. Since these terms are provided merely for the purpose of distinguishing the components from each other, they do not limit the nature, sequence or order of the components. It will be understood that when an element is referred to as being "connected" or "coupled" to another element, it can be directly connected or coupled to the other element or be connected to or coupled to another element, having the other element intervening therebetween.

Elements performing identical functions to elements, which are included in any one exemplary embodiment, will be referred to using the same names in other exemplary embodiments. Unless otherwise specified, the descriptions provided in any one exemplary embodiment may be applicable to exemplary embodiments to be described hereinafter, and repeated descriptions will be omitted.

An image acquisition device 10 according to an embodiment is a device that enables a portable terminal to acquire information on a target.

For example, the target may be skin, and an image of the target may be transmitted through an optical device, such as a camera, which may be provided in the portable terminal.

In the present specification, a description will be given of the image acquisition device 10 that enables the camera of the portable terminal to acquire an image of the skin condition, i.e., the skin, from light radiated to the skin as the target, and diagnoses and analyzes the characteristics of the skin measured through a sensor by making direct contact with the skin.

FIG. 1 is a perspective view illustrating the image acquisition device 10 according to the embodiment.

Referring to FIG. 1, the image acquisition device 10 according to the embodiment may include a body 1000 and a terminal mounting attachment 2000.

The body 1000 may be a part that is in contact with the surface of the target to measure the state or characteristics of the target.

The terminal mounting attachment 2000 may be compatibly attached to various types of portable terminals, and may allow the body 1000 to be detachably coupled thereto.

As described above, since the image acquisition device 10 is attached to the portable terminal in a form in which the body 1000 and the terminal mounting attachment 2000 are coupled to each other, an image of the target is acquired through the camera provided in the portable terminal. In addition, the image acquisition device 10 may make direct contact with the skin to diagnose and analyze the characteristics of the skin measured through the sensor, and transmit this information to the portable terminal.

Therefore, a user using the image acquisition device 10 can diagnose, measure, and analyze the state or characteristic of the target without time or location restrictions.

Figure 2:
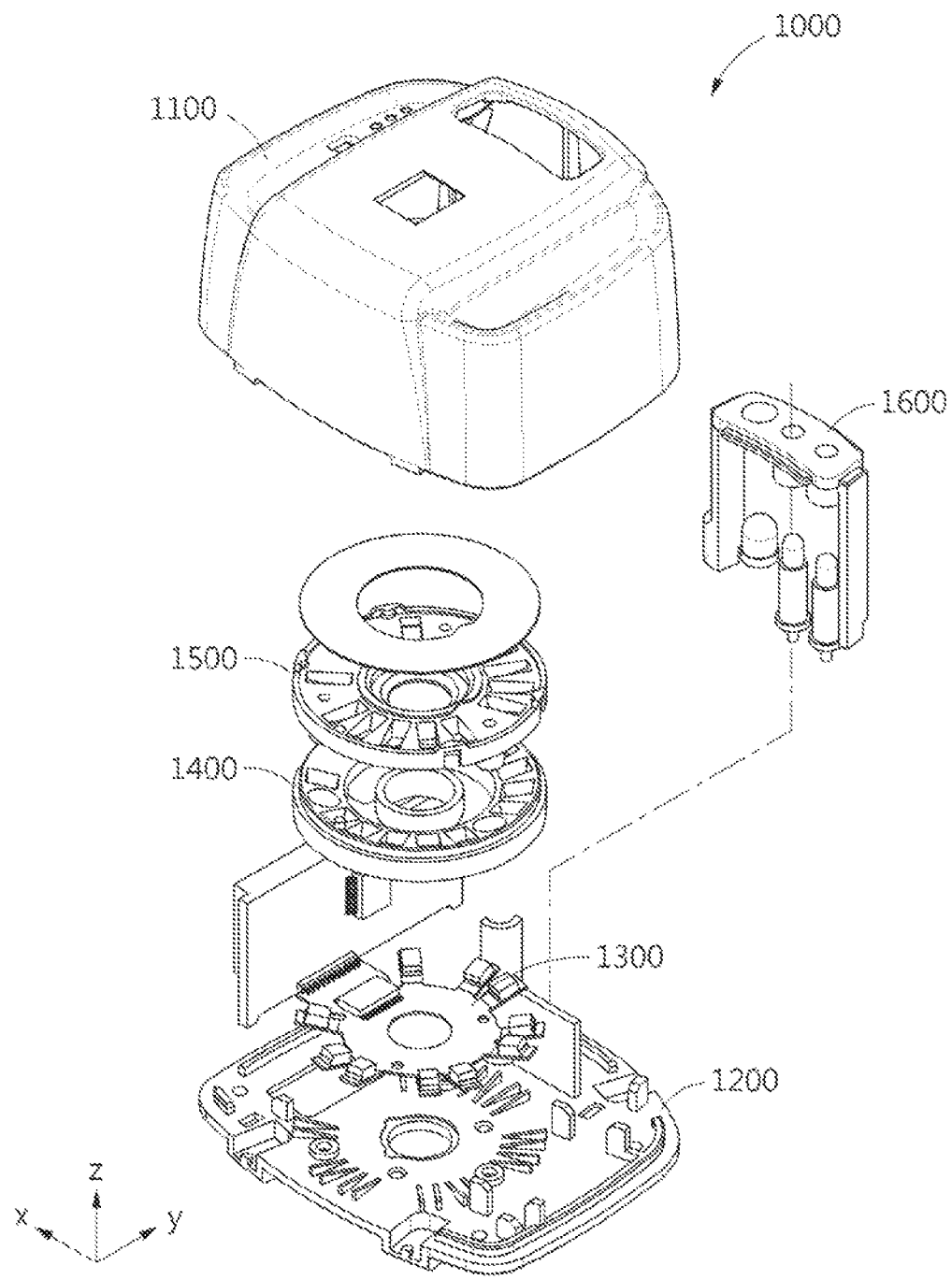
FIG. 2 is an exploded view illustrating a body of the image acquisition device.

FIG. 2 is an exploded view illustrating the body 1000 of the image acquisition device 10.

Referring to FIG. 2, the body 1000 may include an upper body part 1100, a lower body part 1200, a substrate 1300, a light source angle forming part 1400, a film receiving part 1500, and a measurement module 1600.

In addition, each of the upper body part 1100, the lower body part 1200, the substrate 1300, the light source angle forming part 1400, and the film receiving part 1500 may have an opening in the center thereof. These respective openings may be arranged to form a concentric circle when assembling each component. This may be a passage for a light beam to enter a camera lens provided in the portable terminal.

The upper body part 1100 and the lower body part 1200 may be referred to as a housing constituting the exterior of the body 1000, and may be detachably coupled to each other.

A first opening that allows a light beam to be emitted from a light source to the outside through the first opening or to pass through a transparent material through the first opening may be formed in the vicinity of the center of the upper body part 1100.

Therefore, the light beam from the light source may be directly exposed to the target, and may be reflected from the target and directed to the camera lens.

A second opening that allows a portion of the measurement module 1600 to be coupled to the second opening to protrude to the outside from the second opening may be formed in the vicinity of the first opening of the upper body part 1100.

Therefore, the portion of the measurement module 1600 may make direct contact with the target.

The lower body part 1200 may be fixedly coupled to the upper body part 1100.

In addition, a plurality of fixing elements may be provided at a side portion of the lower body part 1200 to allow the body 1000 to be mounted to the terminal mounting attachment 2000 by the fixing elements. For example, the plurality of fixing elements may be hooks or tension protrusions.

A seat part 1210 that allows the substrate 1300 to be placed thereon may be formed on the lower body part 1200. A plurality of seat parts 1210 may be provided and may be configured as a plurality of triangular ribs.

The substrate 1300 is provided with a plurality of light sources 1320. Each of the light sources 1320 may be seated on an associated one of the seat parts 1210 formed on the lower body part 1200.

The light source angle forming part 1400 may be assembled on the substrate 1300 so that light paths of the plurality of light sources 1320 provided on the substrate 1300 intersect with each other.

The film receiving part 1500 may be assembled on the light source angle forming part 1400, and may receive a polarizing film therein.

An image acquisition module of the image acquisition device 10 according to the embodiment, which will be mentioned below, refers to a configuration including the seat parts 1210, the substrate 1300, and the light source angle forming part 1400, and structural and functional features thereof will be described in detail with reference to FIGS. 3 and 4.

The measurement module 1600 may be fixed to the front of the lower body part 1200 at a position inside the body 1000. In addition, a portion of the measurement module 1600 may be coupled to the second opening of the upper body part 1100 to protrude to the outside from the second opening.

Structural and functional features of the measurement module 1600 will be described in detail below with reference to FIGS. 5 and 6.

Figure 3:
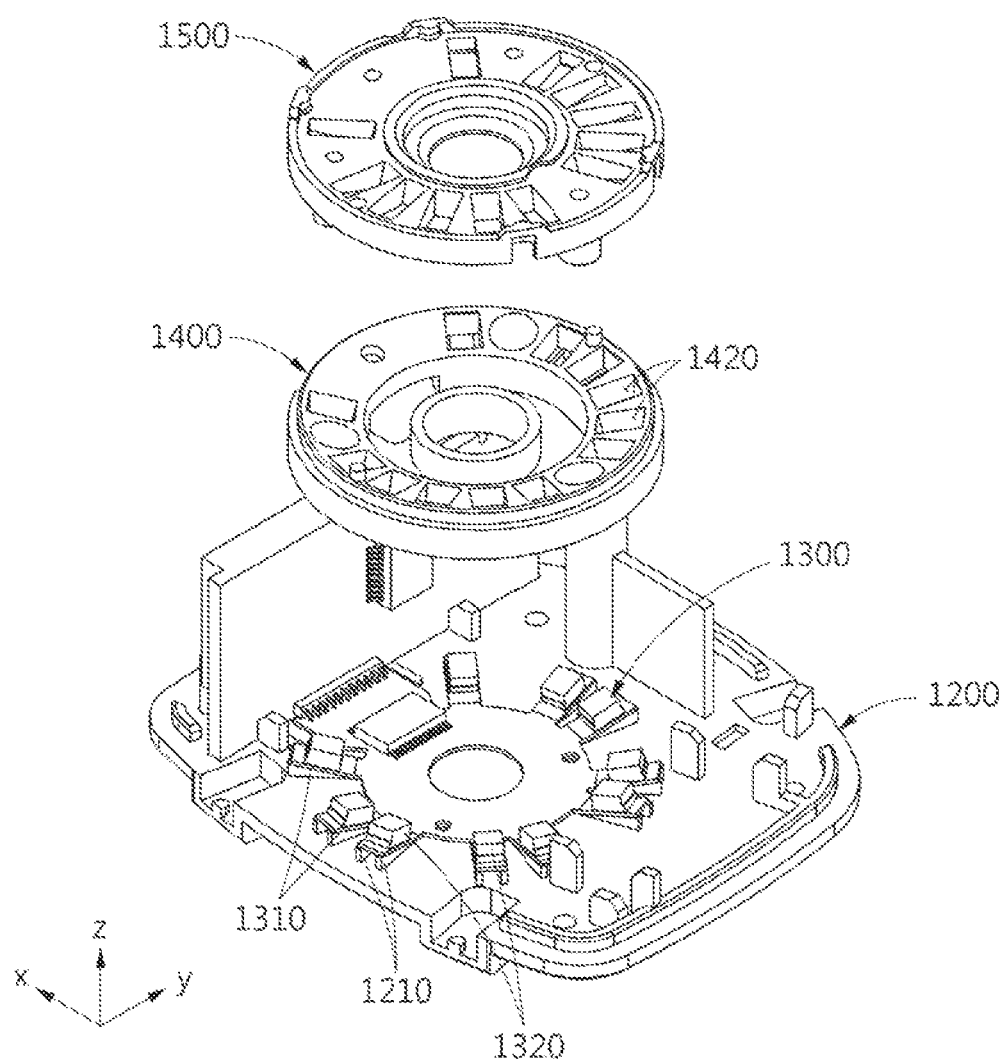
FIG. 3 is a partial exploded view illustrating an image acquisition module.

FIG. 3 is a partial exploded view illustrating the image acquisition module.

The image acquisition module may be a part for measuring the state of the target.

The image acquisition module may be a configuration including the seat parts 1210, the substrate 1300, and the light source angle forming part 1400.

The seat parts 1210 may be the plurality of ribs formed on the lower body part 1200. Each of the ribs may be formed at a position corresponding to an associated one of the plurality of light sources 1320 of the substrate 1300.

The plurality of seat parts 1210 may be circumferentially arranged adjacent to each other around the opening formed in the lower body part 1200. The seat parts 1210 may be disposed to extend in a circumferential direction from the center of the opening when viewed in a plan view, and may have a triangular cross-section when viewed in a side view. In other words, the seat parts 1210 may have a shape that increases in height from the center to the periphery. The angle of the light sources 1320 may be adjusted in response to the amount of change in the height of the seat parts 1210.

The substrate 1300 may include a first substrate and a second substrate that are each provided in the form of a planar plate and are electrically connected to each other.

Specifically, the first substrate may be provided with a control element, and the second substrate may be provided with the plurality of light sources 1320 on an outer peripheral portion thereof at uniform or non-uniform intervals. In this case, the light sources 1320 may be LEDs.

The light sources 1320 may be provided on the second substrate so that respective light paths thereof are parallel to each other.

In addition, the first substrate and the second substrate may be disposed at respective positions inside the main body 1000. The first substrate may be disposed vertically with respect to the lower body part 1200, and the second substrate may be disposed on the seat parts 1210 provided on the lower body part 1200.

In this case, the outer peripheral portion of the second substrate may be in contact with the seat parts 1210 so that each of the light sources 1320 is disposed at a position corresponding to an associated one of the seat parts 1210.

The light source angle forming part 1400 may include an inclined surface 1410 and a through-hole 1420.

Inclined surfaces 1410 may be circumferentially formed in a chamfered shape on a lower portion of the light source angle forming part 1400.

Specifically, the angle of each of the inclined surfaces 1410 of the light source angle forming part 1400 may correspond to an angle formed by an inclined plane of each of the seat parts 1210. The angle of the second substrate may be adjusted by the inclined surfaces 1410.

A plurality of through-holes 1420 may be provided, and may be circumferentially arranged adjacent to each other along an outer peripheral portion of the light source angle forming part 1400 around the opening formed in light source angle forming part 1400.

Specifically, each of the through-holes 1420 of the light source angle forming part 1400 may be formed at a position corresponding to an associated one of the seat parts 1210 or the light sources 1320. Therefore, the light source angle forming part 1400 may be coupled to the substrate 1300 so that the light sources 1320 passes through the through-holes 1420 while the light paths of the light sources are not blocked by the light source angle forming part 1400.

In this case, each of the through-holes 1420 may be formed to have a size that allows each of the light sources 1320 to pass through but prevents each outer peripheral portion 1310 of the substrate 1300 from passing through. Therefore, the respective outer peripheral portions 1310 of the substrate 1300 may be fixed between the light source angle forming part 1400 and the seat parts 1210.

The image acquisition module may further include the film receiving part 1500.

As in the case of the light source angle forming part 1400, the film receiving part 1500 may have a plurality of through-holes formed along an outer peripheral portion of the film receiving part 1500. In addition, a polarizing film may be received in an upper portion of the film receiving part 1500.

Each of the through-holes may be formed at a position corresponding to an associated one of the light sources 1320. Therefore, the film receiving part 1500 may be mounted on the light source angle forming part 1400 so that the light beams from the light sources 1320 pass through the polarizing film through the through-holes while the light paths of the light sources 1320 are not blocked.

Hereinafter, a method of assembling the image acquisition module of the image acquisition device 10 according to the embodiment will be described in detail with reference to FIG. 4.

FIG. 4a illustrates that the lower body part 1200, the substrate 1300, and the light source angle forming part 1400 are provided to assemble the image acquisition module of the image acquisition device 10 according to the embodiment.

Referring to FIG. 4a, the image acquisition module may be assembled in the order of the lower body part 1200, the substrate 1300, and the light source angle forming part 1400. In addition, the film receiving part 1500 may be assembled on the light source angle forming part 1400.

As described above, the lower body part 1200 may be provided with the triangular-shaped seat parts 1210.

Although omitted from the substrate 1300 illustrated in FIGS. 4a to 4c, the plurality of light sources 1320 may be provided on the outer peripheral portions 1310 of the planar plate-shaped substrate 1300.

The light source angle forming part 1400 may have the inclined surfaces 1410 and the through-holes 1420 on the lower portion thereof.

FIG. 4b illustrates that the planar plate-shaped substrate 1300 is provided on the seat parts 1210 formed on the lower body part 1200.

Referring to FIG. 4b, the substrate 1300 may be provided on the lower body part 1200 so that the outer peripheral portions thereof are in contact with the seat parts 1210. In this case, the substrate 1300 may be disposed on the seat parts 1210 so that the light paths of the light sources 1320 are vertical.

FIG. 4c illustrates that the outer peripheral portions of the substrate 1300 are bent by the seat parts 1210 and the light source angle forming part 1400.

Referring to FIG. 4c, after the light source angle forming part 1400 is disposed on the substrate 1300, the light source angle forming part 1400 may be coupled to the substrate 1300 so that the entire lower portion thereof, i.e., even the inclined surfaces 1410, is in contact with the substrate 1300.

Specifically, the substrate 1300 may be made of a material that is deformable by pressure. The light source angle forming part 1400 may change the angle of the substrate 1300 initially provided in the form of a planar plate by pressing the substrate 1300 with respect to the seat parts 1210. The outer peripheral portions of the substrate 1300 positioned between the seat parts 1210 and the inclined surfaces 1410 may be bent according to the inclination of the seat parts 1210 or the inclined surfaces 1410. In other words, the angle of the outer peripheral portions of the substrate 1300 may be adjusted by pressure in response to the angle of the seat parts 1210 or the inclined surfaces 1410, thereby adjusting the angle of the light sources 1320 provided on the outer peripheral portions 1310.

Figure 4:
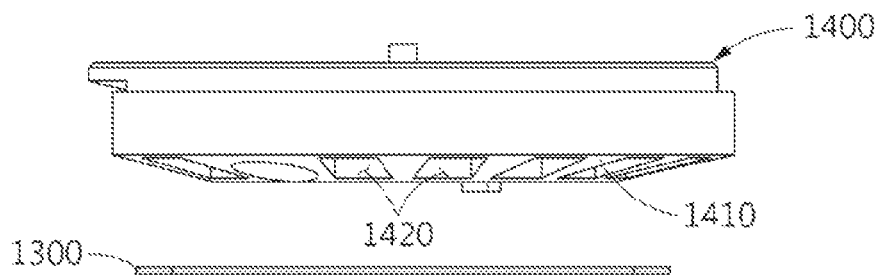
FIG. 4 illustrates a method of assembling the image acquisition module.
Figure 4:
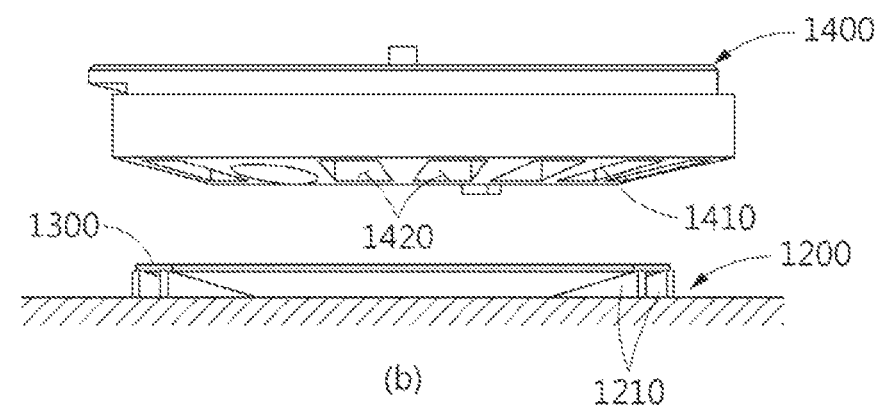
Figure 4:
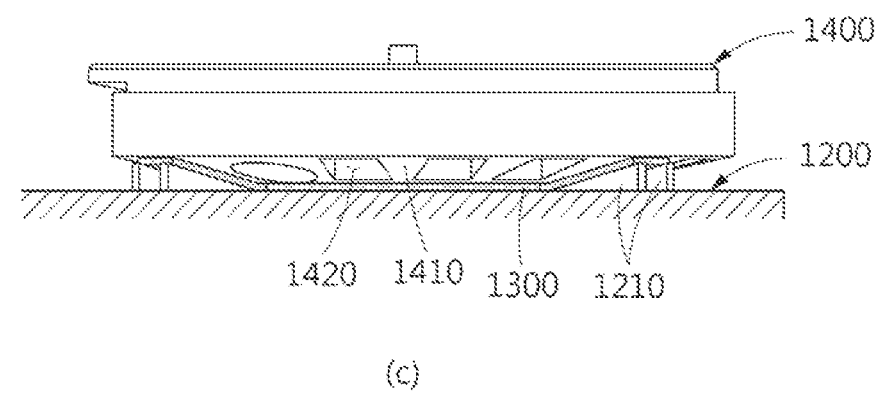

In addition, although not illustrated in FIG. 4, the film receiving part 1500 may be disposed on the light source angle forming part 1400 and coupled to the lower body part 1200 together with the substrate 1300 and the light source angle forming part 1400.

Specifically, at least two fastening holes may be formed in the film receiving part 1500. Fastening holes may also be formed in each of the lower body part 1200 and the light source angle forming part 1400 at positions corresponding to the at least two fastening holes.

Fixing bolts provided from the lower portion of the lower body part 1200 may be fastened to the fastening holes formed in the film receiving part 1500 by passing through the fastening holes formed in the lower body part 1200 and the light source angle forming part 1400.

As a result, the angle of the light sources 1320, which are initially provided on the substrate 1300 so that the light paths thereof are parallel to each other, may be adjusted so that the light paths of the light sources 1320 intersect with each other toward one focal point while the outer peripheral portions 1310 are bent inward by the seat parts 1210 or the light source angle forming part 1400. In addition, the angle of the light sources may be maintained in an adjusted state by fastening the fixing bolts from the lower body part 1200 to the film receiving part 1500.

Finally, the upper body part 1100 may be coupled to the lower body part 1200, thereby completing the assembly of the body 1000. Therefore, the light beams from the light sources 1320 may pass through the polarizing film received in the film receiving part 1500 and then be focused toward the first opening formed in the upper body part 1100.

The light beams passing through the first opening may be reflected after reaching the surface of the target. The light beams reflected back to the inside of the body 1000 again pass through sequentially the openings centrally provided in the film receiving part 1500, the light source angle forming part 1400, the substrate 1300, and the lower body part 1200 to finally be incident on the camera lens provided in the portable terminal. The camera may acquire an image of the target by the incident light beams. The acquired image may be output to a screen of the portable terminal, so that the user can check the state of the target through the acquired image.

Figure 5:
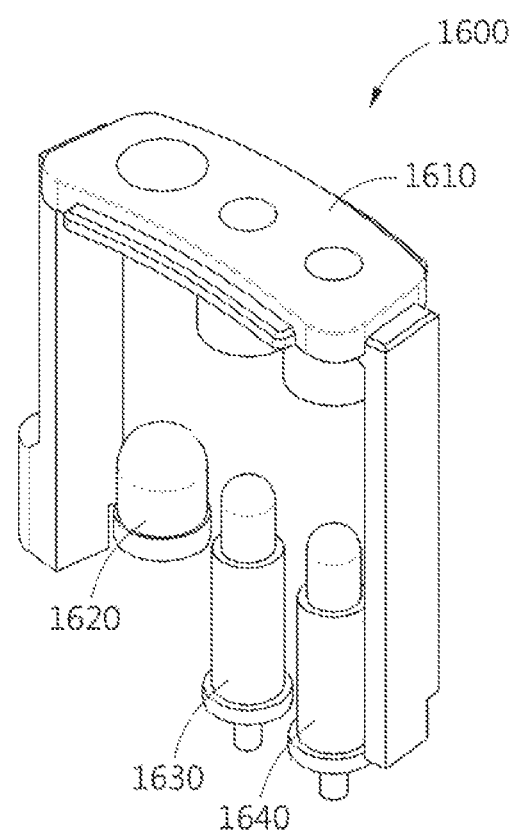
FIG. 5 is an exploded view illustrating a measurement module.

FIG. 5 is an exploded view illustrating the measurement module 1600.

Figure 6:
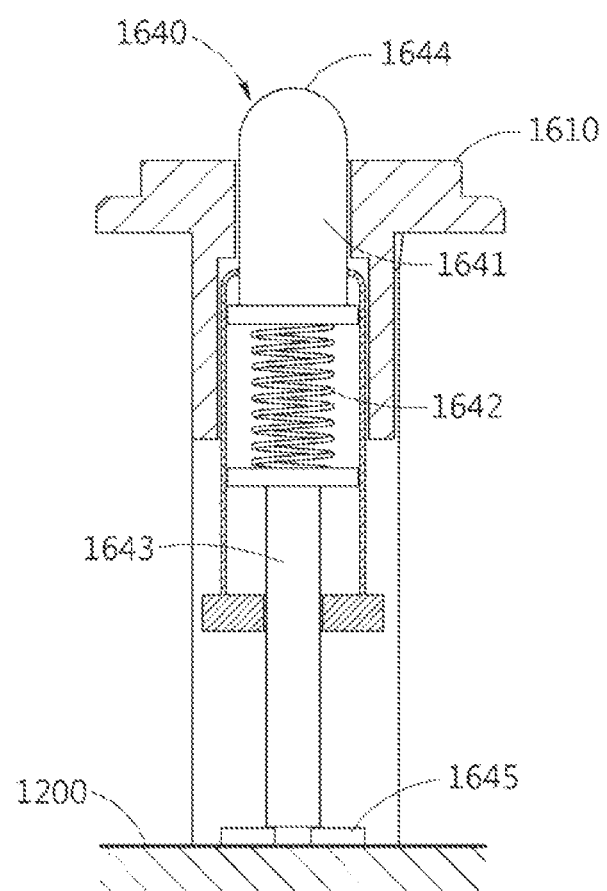
FIG. 6 is a sectional view illustrating a third measuring part.

FIG. 6 is a sectional view illustrating a third measuring part 1640.

The measurement module 1600 may be a part for measuring various characteristics such as temperature, oil/moisture, and elasticity of the target. As described above, the measurement module 1600 may be disposed on the front of the lower body part 1200 at a position inside the body 1000, and a portion of the measurement module 1600 may protrude outward through the second opening of the upper body part 1100 in order to measure various characteristics of the target.

Specifically, the measurement module 1600 may include a base 1610, a first measuring part 1620, a second measuring part 1630, and the third measuring part 1640.

The base 1610 may support the first measuring part 1620, the second measuring part 1630, and the third measuring part 1640, with a lower end thereof fixed to the body.

The base 1610 may have an upper portion coupled to the second opening formed in the upper body part 1100. In addition, at least one coupling hole may be formed in the upper portion of the base 1610, so that a contact member of each of the first measuring part 1620, the second measuring part 1630, and the third measuring part 1640 may protrude to the outside of the body 1000 through the coupling hole.

The first measuring part 1620, the second measuring part 1630, and the third measuring part 1640 may make direct contact with the target to measure the characteristics of the target.

The first measuring part 1620 may measure the temperature of the target, and may be mounted to the base 1610 through as associated one of a plurality of coupling holes formed in the base 1610.

Specifically, the first measuring part 1620 may include a first contact member and a temperature sensor.

The first contact member may protrude to the outside of the upper body part 1100 by passing through the base 1610 and may make direct contact with the target. In this case, the first contact member may be formed in a dome shape with a smooth surface.

The temperature sensor may be located on the surface or inside of the first contact member, and may measure the temperature of the target. In this case, the first contact member may be made of a material having high thermal conductivity for accurate temperature measurement of the temperature sensor.

The second measuring part 1630 may measure the oil/moisture of the target, and may be mounted to the base 1610 through an associated one of the coupling holes of the base 1610 so as to be disposed adjacent to the first measuring part 1620.

Specifically, the second measuring part 1630 may include a second contact member, an oil/moisture sensor, an elastic member, and a support member.

The second contact member may protrude to the outside of the upper body part 1100 by passing through the base 1610 and may make direct contact with the target. The second contact member may also be formed in a dome shape with a smooth surface.

The oil/moisture sensor may be located on the surface or inside of the second contact member, and may measure the oil/moisture of the target.

The elastic member may have a first end coupled to a lower end of the second contact member and a second end coupled to an upper end of the support member.

The support member may have an upper portion coupled to a lower end of the elastic member, and a lower portion in contact with the lower body part 1200.

Referring to FIG. 6, the third measuring part 1640 may measure the elasticity of the target, and may be mounted to the base 1610 through an associated one of the coupling holes of the base 1610 so as to be disposed adjacent to the first measuring part 1620 or the second measuring part 1630.

Specifically, the third measuring part 1640 may include a third contact member 1641, an elastic member 1642, a support member 1643, and an elasticity sensor 1645.

The third contact member 1641 may protrude to the outside of the upper body part 1100 by passing through the base 1610 and may make direct contact with the target. The third contact member 1641 may also be formed in a dome shape with a smooth surface.

The elastic member 1642 may have a first end coupled to a lower end of the third contact member 1641 and a second end coupled to an upper end of the support member 1643.

The support member 1643 may have an upper portion coupled to a lower end of the elastic member 1642, and a lower portion in contact with the elasticity sensor 1645.

The elasticity sensor 1645 may be provided on the lower body part 1200, and may measure the elasticity of the target.

The elasticity sensor 1645 may receive pressure through the support member 1643, the pressure being generated when the third contact member 1641 makes contact with the target. The elasticity sensor 1645 may measure the elasticity of the target from the pressure value.

The measurement module 1600 according to the above-described embodiment has been described as a configuration in which the first measuring part 1620, the second measuring part 1630, and the third measuring part 1640 individually measure various characteristics of the target, such as temperature, oil/moisture, and elasticity. However, the measurement module 1600 may be provided with an integrated third measuring part 1640 so that one measuring part can simultaneously measure the characteristics of the target that can be measured by the first measuring part 1620, the second measuring part 1630, and the third measuring part 1640.

In such a case, referring back to FIG. 6, the third measuring part 1640 may further include a first sensor 1644.

The first sensor 1644 may be provided on the surface or inside of the third contact member 1641, and may make direct contact with the surface of the target. In addition, the first sensor 1644 may be provided as a temperature and oil/moisture sensor 1644 to measure the temperature or the oil/moisture of the target.

A second sensor 1645 may be located at a lower end of the support member 1643, and may be provided as an elasticity sensor 1645. In addition, the second sensor 1645 may measure the elasticity of the target from the pressure transmitted to the support member 1643 when the contact member 1641 makes contact with the target.

Therefore, the measurement module 1600 including the integrated measuring part 1640 has the effect of simultaneously measuring various characteristics of the target through one contact part.

As a result, the image acquisition device 10 having the above-described constituent elements can easily diagnose and analyze the state of the target through the image acquisition module, and can easily measure characteristics such as temperature, oil/moisture, or elasticity of the target through the measurement module.

In addition, anyone using the image acquisition device 10 can easily diagnose, measure, and analyze the state or characteristic of the target without time or location restrictions.

Although the present disclosure is described with reference to specific items such as specific structural elements, to merely some embodiments, and to drawings, such specific details disclosed herein are merely representative for purposes of helping more comprehensive understanding of the present disclosure. The present disclosure, however, is not limited to only the example embodiments set forth herein, and those skilled in the art will appreciate that the present disclosure can be embodied in many alternate forms. For instance, suitable results may be achieved if the described techniques are performed in a different order, and/or if components in a described system, architecture, device, or circuit are combined in a different manner and/or replaced or supplemented by other components or their equivalents. Accordingly, the present disclosure is intended to cover not only the exemplary embodiments, but also various alternatives, modifications, equivalents, and other embodiments that may be included within the spirit and scope of the present disclosure as defined by the appended claims.

The invention claimed is:

1. An image acquisition device comprising:
   a body;
   a seat part provided on a lower part of the body;
   a substrate disposed on the seat part inside the body and having a plurality of light sources; and
   a light source angle forming part disposed on the substrate inside the body,
   wherein the seat part is formed at a position corresponding to each of the plurality of light sources, and has a triangular cross-section,
   wherein the plurality of light sources are disposed on an outer peripheral portion of the substrate,
   wherein the substrate is initially provided on the seat part in the form of a planar plate, and the outer peripheral portion of the substrate positioned between the seat part and the light source angle forming part is bent according to inclination of the seat part as the light source angle forming part presses the substrate, and
   wherein the outer peripheral portion of the substrate is bent by the seat part or the light source angle forming part so that light paths of the light sources intersect with each other.

2. The image acquisition device of claim 1, wherein the light source angle forming part has an inclined surface corresponding to each seat part, and a through-hole allowing each of the plurality of light sources to pass therethrough.

3. A method of manufacturing an image acquisition device, the method comprising:
   providing a lower part of the body provided with a triangular seat part;
   providing, on the seat part, a planar substrate provided with a plurality of light sources disposed on an outer peripheral portion of the substrate;
   providing, on the substrate, a light source angle forming part having an inclined surface; and
   bending the outer peripheral portion of the substrate positioned between the seat part and the inclined surface according to inclination of the seat part as the light source angle forming part presses the substrate so that the light sources of the substrate is directed toward one focal point with respect to the seat part.

4. The method of claim 3, further comprising:
   providing a film receiving part on the light source angle forming part and fastening the film receiving part to the lower part of the body together with the light source angle forming part and the substrate.

5. An image acquisition device comprising:
   an image acquisition module configured to measure a state of a target;
   a measurement module configured to measure at least one target characteristic of elasticity, temperature, and oil/moisture; and
   a body in which the image acquisition module and the measurement module are mounted,
   wherein a portion of the measurement module protrudes to outside of the body and measures the characteristic of the target by making direct contact with the target,
   wherein the image acquisition module comprises:
   a body;
   a seat part provided on a lower part of the body;
   a substrate disposed on the seat part inside the body and having a plurality of light sources; and
   a light source angle forming part disposed on the substrate inside the body,
   wherein the seat part is formed at a position corresponding to each of the plurality of light sources, and has a triangular cross-section,
   wherein the plurality of light sources are disposed on an outer peripheral portion of the substrate,
   wherein the substrate is initially provided on the seat part in the form of a planar plate, and the outer peripheral portion of the substrate positioned between the seat part and the light source angle forming part is bent according to inclination of the seat part as the light source angle forming part presses the substrate, and
   wherein the outer peripheral portion of the substrate is bent by the seat part or the light source angle forming part so that light paths of the light sources intersect with each other.

6. The image acquisition device of claim 5, wherein the measurement module comprises:
   a base fixed to the body;
   a contact member passing through the base and configured to make direct contact with the target and having a first sensor therein;
   an elastic member having a first end coupled to a lower end of the contact member; and
   a support member having a first end coupled to a second end of the elastic member and having a second end in contact with a second sensor,
   wherein the first sensor measures the temperature or the oil/moisture of the target, and the second sensor measures the elasticity of the target from pressure transmitted through the support member when the contact member makes contact with the target.

7. The image acquisition device of claim 5, wherein the measurement module comprises:
   a base fixed to the body;
   a first measuring part mounted to the base and configured to measure the temperature of the target;
   a second measuring part mounted to the base, disposed adjacent to the first measuring part, and configured to measure the oil/moisture of the target; and a third measuring part mounted to the base, disposed adjacent to the first measuring part or the second measuring part, and configured to measure the elasticity of the target, wherein each of the first measuring part, the second measuring part, and the third measuring part measures the characteristic of the target by making contact with the target.

8. The image acquisition device of claim 7, wherein the first measuring part comprises a first contact member protruding to outside of an upper part of the body and configured to make direct contact with the target, and the first contact member is provided with a temperature sensor to measure the temperature of the target.

9. The image acquisition device of claim 7, wherein the second measuring part comprises:

a second contact member protrudes to outside of an upper part of the body by passing through the base and configured to make direct contact with the target;

an elastic member having a first end coupled to a lower end of the second contact member; and a support member to which a second end of the elastic member is coupled, wherein the second contact member is provided with an oil/moisture sensor to measure the oil/moisture of the target.

10. The image acquisition device of claim 7, wherein the third measuring part comprises:

a third contact member protruding to outside of an upper part of the body by passing through the base and configured to make direct contact with the target;

an elastic member having a first end coupled to a lower end of the third contact member; and a support member having a first end coupled to a second end of the elastic member and a second end in contact with a pressure sensor, wherein the elasticity of the target is measured from pressure generated when the third contact member makes contact with the target is transmitted to the pressure sensor through the support member.

* * * * *